(12) United States Patent
Adler et al.

(10) Patent No.: US 9,056,173 B2
(45) Date of Patent: Jun. 16, 2015

(54) DRY POWDER INHALER

(75) Inventors: Dan Adler, Haifa (IL); Amnon Kritzman, Karkur (IL); Arie Holtz, Jerusalem (IL)

(73) Assignee: AESPIRA LTD., MoshavShdema (IL)

( * ) Notice: Subject to any disclaimer, the term of this patent is extended or adjusted under 35 U.S.C. 154(b) by 464 days.

(21) Appl. No.: 13/575,908

(22) PCT Filed: Jan. 30, 2011

(86) PCT No.: PCT/IL2011/000103
§ 371 (c)(1),
(2), (4) Date: Oct. 3, 2012

(87) PCT Pub. No.: WO2011/080747
PCT Pub. Date: Jul. 7, 2011

(65) Prior Publication Data
US 2013/0042864 A1    Feb. 21, 2013

(30) Foreign Application Priority Data

Jan. 27, 2010   (IL) .......................................... 203561

(51) Int. Cl.
| *A61M 15/00* | (2006.01) |
| *A61M 11/00* | (2006.01) |
| *A61M 16/00* | (2006.01) |
| *B05D 7/14* | (2006.01) |
| *B65D 83/06* | (2006.01) |
| *A61M 15/06* | (2006.01) |

(52) U.S. Cl.
CPC ....... *A61M 15/0028* (2013.01); *A61M 15/0091* (2013.01); *A61M 15/06* (2013.01); *A61M 2202/064* (2013.01); *A61M 11/003* (2013.01); *A61M 15/0003* (2013.01); *A61M 15/0008* (2013.01); *A61M 15/0043* (2013.01)

(58) Field of Classification Search
USPC ............. 128/200.24, 203.15, 203.21, 203.12; 482/13; 604/58, 48, 73; 600/539
See application file for complete search history.

(56) References Cited

U.S. PATENT DOCUMENTS

| 3,669,113 A | 6/1972 | Altounyan et al. |
| 5,699,789 A | 12/1997 | Hendricks |
| 2001/0035184 A1 | 11/2001 | Schuler et al. |
| 2003/0159694 A1 | 8/2003 | McNaughton |
| 2009/0095294 A1 | 4/2009 | Smyth et al. |

OTHER PUBLICATIONS

International Search Report of PCTIL2011/000103 dated Jun. 24, 2011.

*Primary Examiner* — Tan-Uyen (Jackie) T Ho
*Assistant Examiner* — Mark Wardas
(74) *Attorney, Agent, or Firm* — Sughrue Mion, PLLC

(57) ABSTRACT

The present invention provides a dry-powder inhaler device comprising: a casing; an air inlet located at a first terminus of the casing; a powder delivery port located at a second terminus of the casing, which is positioned distal to the air inlet; and an elongated assembly located within an interior of the casing. A first terminus is located proximally to the air inlet, a second terminus is located proximally to the powder delivery port, and the assembly is fitted within the casing such that said assembly partially rotates therein about a single axis. The assembly has at least one compartment containing dry-powder, which is located proximally to the second terminus. The compartment with a dry-powder comprises a porous structure encasing the dry-powder; whereby airflow through the device causes the assembly to partially rotate within the casing about a single axis and release the dry-powder in the airflow.

18 Claims, 5 Drawing Sheets

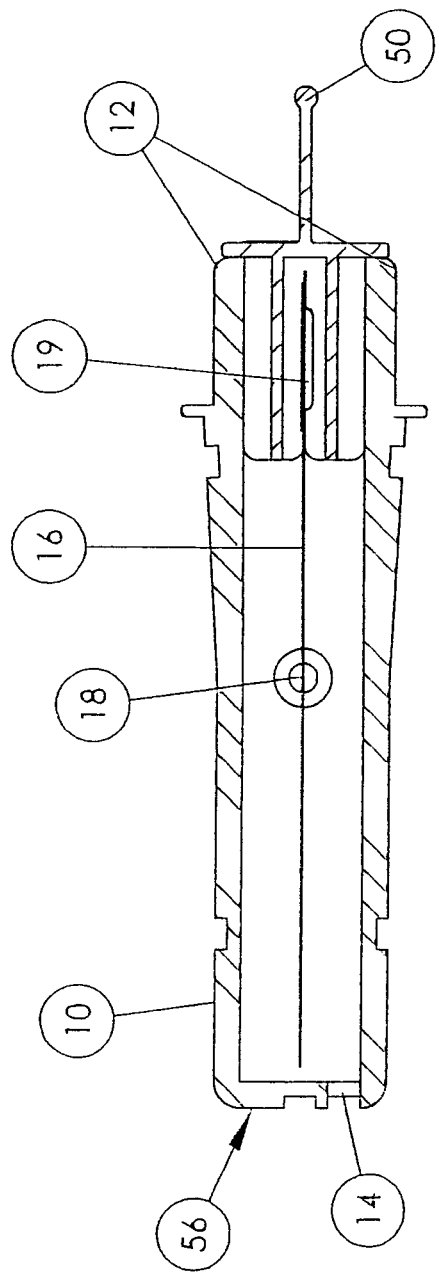
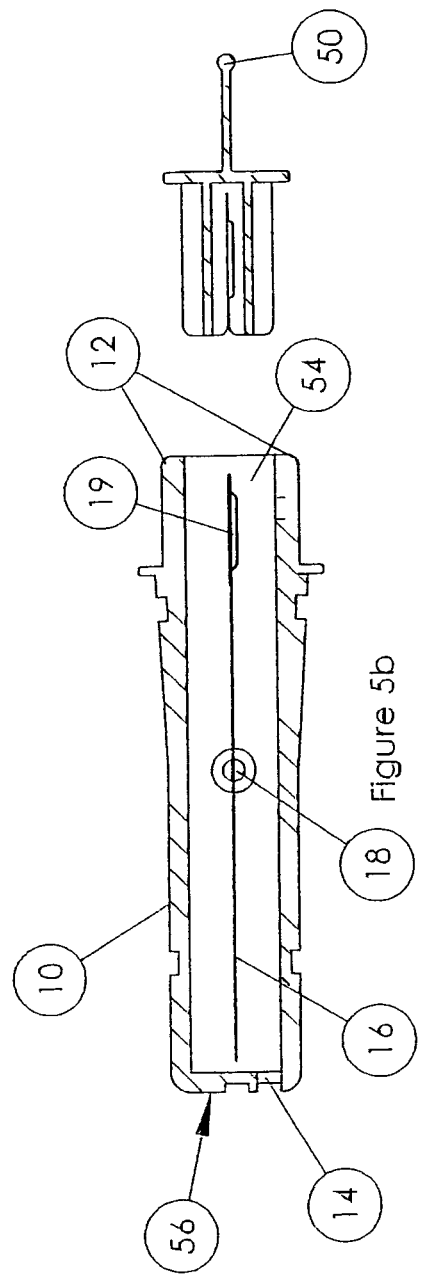

US 9,056,173 B2

DRY POWDER INHALER

CROSS REFERENCE TO RELATED APPLICATIONS

This application is a National Stage of International Application No. PCT/IL2011/000103 filed Jan. 30, 2011, claiming priority based on Israeli Patent Application No. 203561 filed Jan. 27, 2010, the contents of all of which are incorporated herein by reference in their entirety.

BACKGROUND OF THE INVENTION

Numerous drugs, medications and other substances are inhaled into the lungs for rapid absorption in the blood stream and systemic delivery, or alternatively for therapeutic treatment locally. Inhaled drugs are typically either in aerosolized or powder form. In either case, the delivered agent should have a particle or droplet nuclei size that is 5 microns or less in order to reach the terminal ramifications of the respiratory tree.

Such small particles are, however, thermodynamically unstable due to their high surface area to volume ratio, which provides significant excess surface free energy and encourages particles to agglomerate. Agglomeration of the particles and adherence of the particles to the internal surfaces of the inhaler result in delivery of particles too large in size, delivery of a lower dose, due to particle adherence to the interior surfaces of the inhaler, poor flow and non-uniform dispersion, which results in the delivery of a varying dosage. In addition, as noted above, many dry powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

Further, the hygroscopic nature of many dry powder drugs may also require that the device be cleansed (and dried) at periodic intervals.

Therefore, there remains a need for a dry-powder inhalation device that facilitates the dispersion of active drug powder and delivers a consistent dose to the deep lung and is not plagued by the above-described limitations.

SUMMARY OF THE INVENTION

This invention provides, in some embodiments, a dry-powder inhaler device comprising:
a casing;
an air inlet located at a first terminus of said casing;
a powder delivery port located at a second terminus of said casing, which powder delivery port is positioned distal to said air inlet; and
an elongated assembly located within an interior of said casing, wherein:
  a first terminus of said assembly is located proximally to said air inlet;
  a second terminus of said assembly is located proximally to said powder delivery port;
  said assembly is fitted within said casing such that said assembly partially rotates within said casing about a single axis; and
  said assembly comprises at least one compartment containing a dry-powder, wherein;
  said compartment containing a dry-powder is located proximally to said second terminus of said assembly; and
  said compartment containing a dry-powder comprises a porous structure encasing said dry-powder;
whereby airflow through said device causes said assembly to partially rotate within said casing about a single axis and dry-powder is thereby released from said compartment and becomes entrained in said airflow.

In another embodiment, this invention provides a kit comprising at least one dry-powder inhaler device of the invention and one or more mouthpieces, which mouthpieces may attach to the powder delivery port of the device.

In some embodiments, the invention provides a method of dispensing dry powder from a device of this invention to cause the assembly therein to partially rotate within the device casing about a single axis and thereby release dry-powder from a compartment therein to become entrained in said airflow, thereby dispensing dry powder from the inhaler.

BRIEF DESCRIPTION OF THE DRAWINGS

FIG. 3*b* shows a cross-sectional view of an embodiment of an assembly of this invention, subsequent to closing the porous compartment.

FIG. 5*a* provides a cross-sectional view of an embodied inhaler of the present invention with the rocker held in place by a cap.

FIG. 5*b* shows a cross-sectional view of an embodied inhaler after removal of the cap.

DETAILED DESCRIPTION OF THE INVENTION

This invention, inter alia, takes advantage of flow energy of inspired air to disperse micronized particles packaged in a dosage form. The present invention provides a novel inhaler device, in which a principle of operation of the device is the production of a beating action within the device, which beating facilitates the release of a dry-powder drug contained in a porous package located within the device.

The inhalers of this invention are dry-powder inhaler devices, comprising a casing, which casing further comprises an air inlet located at a first terminus of said casing and a powder delivery port located at a second terminus of said casing, which powder delivery port is positioned distal to the air inlet.

The term "casing" refers inter alia, to the container comprising the various elements of the device as described herein. The casing may be of any appropriate material, including, in some embodiments, any plastic or other appropriate synthetic material, which may be prepared to conform to the desired structure and will contain or comprise the elements described herein. In some embodiments, the casing may comprise a Polycarbonate or HDPE.

The casing will comprise two openings placed at opposite ends of the casing. One such opening is the air inlet, which inlet is sufficient in size to facilitate air entry and exit therefrom. Another opening in the casing is a powder delivery port, which powder delivery port is positioned at an opposite end of the casing from that of the air inlet.

The powder delivery port is an opening, which opening is larger is size, in terms of overall area, than that of the air inlet.

Figure 1A:
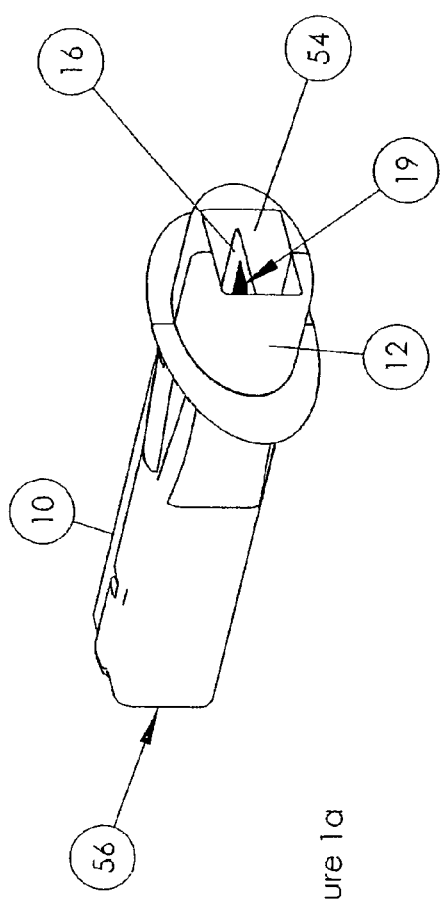
FIG. 1*a* provides an isometric view of an embodiment of an inhaler device of the present invention.

Referring now to FIG. 1a, the inlet 14 is positioned at one terminus of the casing, whereas the powder delivery port 54 is at the opposite end or terminus of the casing.

The casings of this invention may be prepared by any means, and may include for example, designs which comprise two halves of the casing, which halves may be hermetically and permanently sealed, or in some embodiments, the casing may be of a single piece, for example, as prepared by molding, and other conventional means.

In some embodiments, the air inlet is positioned to be off center of a horizontal axis, a vertical axis or a combination thereof of a side of the casing containing the air inlet.

Figure 1B:
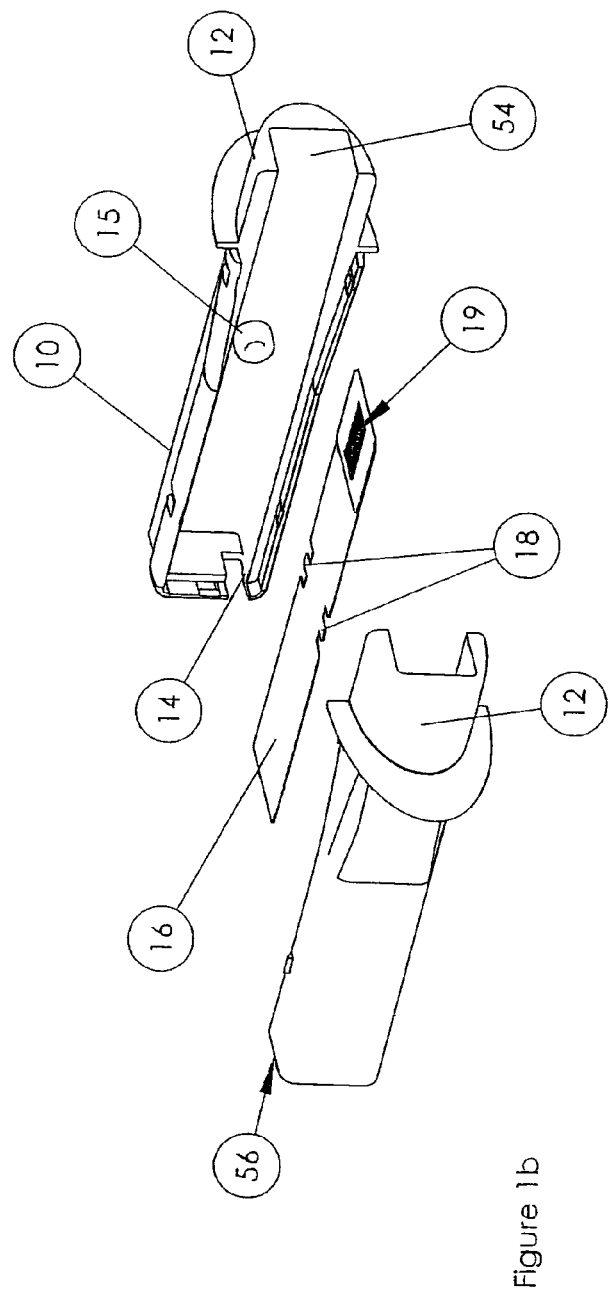
FIG. 1*b* provides an exploded isometric view of an embodiment of an assembled inhaler device of the present invention.

For example, referring to FIGS. 1a and 1b, referring to the side 56 comprising the air inlet 14, as you will note, the air inlet is located in the lower half of side 56, when an imaginary line is drawn across the horizontal midline axis. Similarly, the air inlet is located off-center with respect to an imaginary line drawn across the vertical midline axis.

The casing in the dry-powder inhaler devices of this invention will further comprise an elongated assembly located within an interior of the casing, wherein:
  a first terminus of said assembly is located proximally to said air inlet;
  a second terminus of said assembly is located proximally to said powder delivery port;
  said assembly is fitted within said casing such that said assembly partially rotates within said casing about a single axis; and
  said assembly comprises at least one compartment containing a dry-powder, wherein:
    said compartment containing a dry-powder is located proximally to said second terminus of said assembly; and
    said compartment containing a dry-powder comprises a porous structure encasing said dry-powder;
whereby airflow through said device causes said assembly to partially rotate within said casing about a single axis and dry-powder is thereby released from said compartment and becomes entrained in said airflow.

With reference to the assembly located within the casings of this invention, the assembly is elongated, in that the assembly has a length sufficient that each terminus can abut or strike an interior surface of the casing, when rotated or angled, there-within.

Indeed, the assembly is positioned within the casing such that a first terminus of the assembly is located proximally to the air inlet while a second terminus of said assembly is located proximally to said powder delivery port, such that a long axis of the assembly is oriented in parallel to a long axis of the casing.

In some embodiments, the casing, the assembly, or a combination thereof is substantially rectangular. In some embodiments, the casing, the assembly, or a combination thereof is substantially cuboidal, or in some embodiments, the casing, the assembly, or a combination thereof is substantially columnar, or in some embodiments, the casing, the assembly, or a combination thereof is substantially oval, in shape.

Referring again to FIG. 1b, the long axis of the assembly 16, is oriented in parallel to the long axis of the casing 10.

The assemblies in the inhaler devices of this invention will comprise at least one compartment containing a dry-powder, where the compartment containing a dry-powder comprises a porous structure encasing the dry-powder, and the compartment containing the dry-powder is located proximally to the second terminus of the assembly when positioned within the casings as herein described.

Referring now to FIGS. 1b-3 the assembly 16 comprises at least one compartment 19, located proximally to the second terminus of the assembly, near the powder delivery port 54. According to this aspect, and representing one embodiment, this powder delivery port 54 is partially enclosed by or attached to an ergonomically designed mouthpiece 12.

In some embodiments, the inhaler devices of this invention are suitable for inhalation delivery by mouth, or nasal delivery. According to one aspect, and in one embodiment, the powder delivery port is partially enclosed by or attached to a mouthpiece, or in some embodiments, the delivery port is partially enclosed by or attached to a nosepiece, which enables inhalation delivery via the mouth or nose.

In some embodiments, such choice between nasal or mouth delivery will reflect a consideration of the target area for delivery in the nasopharynx and other regions of the respiratory tree, or the particle size for delivery, or the age of the subject to which the inhaled powder is being administered, or a combination thereof.

In some embodiments, a typical size range for the casing 10 of the present invention is between 5 cm and 15 cm in length, and with height and width dimensions in the 0.5 cm-2 cm range. The length and width of the assembly 16 are set to closer fit the inner dimensions of this casing.

The compartment 19 will comprise a porous structure, such that the dry-powder encased within can exit the compartment through the pores in the porous structure. In some embodiments, most of the compartment will comprise a porous structure. In some embodiments, more than 50% of the area of the compartment will comprise a porous structure, or in some embodiments, more than 60% of the area of the compartment will comprise a porous structure, or in some embodiments, more than 70% of the area of the compartment will comprise a porous structure, or in some embodiments, more than 80% of the area of the compartment will comprise a porous structure, or in some embodiments, more than 85% of the area of the compartment will comprise a porous structure, or in some embodiments, more than 90% of the area of the compartment will comprise a porous structure, or in some embodiments, more than 95% of the area of the compartment will comprise a porous structure, or in some embodiments, more than 95%-98% of the area of the compartment will comprise a porous structure.

In some embodiments, the fact that the compartment comprises a porous structure, may refer to, inter alia, that the compartment is made of a porous material, or in some embodiments, that the compartment incorporates a porous structure adhered to the substrate making up the compartment, and others, as will be appreciated by the skilled artisan. In some embodiments, the term porous structure refers to a structure which contains holes or voids of a particular size or size range, arranged as a compartment, such that a casing or envelope is formed. According to this aspect, and in one embodiment, the casing is sealed or closed, such that a dry-powder is contained there-within, which dry-powder is of a size that can pass through the holes or voids.

In some embodiments, the porous structure may comprise a mesh-like structure or porous pouch.

In some embodiments, the porous structure may be any type of package with appropriately-sized holes. Examples include packages fabricated from netting, woven-style meshes where the holes exist by virtue of the weaving structure (i.e. are located between the threads), perforated materials and laser-perforated materials, etc. The materials may be fabricated from plastic or metals, with the use of materials such as aluminum or aluminized foil, for example. All packages constructed from such materials are herein termed "porous structure" which in turn may make up the "compartment".

In some embodiments, the porous structure may comprise a metal mesh-like compartment. In some embodiments, such metal mesh-like compartment may comprise stainless steel or any other metals such as aluminum, brass, copper, Monel™, nickel, steel and zinc, which will not result in, or will result in minimal static electricity between the powder encased there-within and the pores of the compartment structure. In some embodiments, the compartment may comprise a MicroGrid® Precision Expanded Metal &/or Metal Foil (DEXMET Corporation, Wallingford, Conn. 06492, USA).

In some embodiments, the porous structure may comprise a porous envelope or pouch, which porous envelope or pouch is comprised of a material, such as a polymer or resin, which does not interfere with appropriate dispersion of the powder through the holes or voids contained within the envelope or pouch, upon use of the inhaler device.

In some embodiments, examples of such polymers may include Fluoroplastics such as PTFE, PP, PE, PFEP, PCTFE, PVF, PVDF, PFA and ECTFE; Polyamides such as Nylon 6 and Nylon 6.6, Peek; Polyolefins such as PE and PP; Polyesters such as PET, PETP, PBTP; Polysulfone; Polyvinyl; high temperature plastics such as PTFE, PEEK; and Nylons.

In some embodiments, the porous structure will comprise pores having a pore size ranging from about 20 to about 50 microns, which in some embodiments, is ideally sized for the release of a dry-powder drug having a diameter of about 1-5 microns.

In some embodiments, the pores in said compartment are of a size sufficiently large to enable the exit of the particles. For example, for a 3 micron diameter particle, the pore size may range from about between 6 microns and 150 microns, or in some embodiments, between 10 microns and 80 microns or in some embodiments between 20 microns and 60 microns. The thickness of the porous structure may range from between 40 microns and 240 microns. In some embodiments, the compartment thickness will be greater than the average pore size in the compartment, which in turn may enhance the ability of the compartment to retain the dry powder until use.

In some embodiments, according to this aspect, dry-powder exit from the inhaler devices of this invention is facilitated by the beating action, or abutment of the assembly against an interior surface of the casing, which results in powder egress from the pores of the compartment, wherein when the compartment walls are thicker than the pore diameter, a tunneling effect occurs, resulting in a time-bound exit from the porous compartment. In some embodiments, the tunneling effect also serves to improve the disaggregation that takes place as the particles exit the compartment.

In some embodiments, the assembly will comprise the same material as that of the compartment, or in some embodiments, the assembly will comprise a different material than that of the compartment. In some embodiments, the compartment is contiguous in structure with that of the assembly, or in some embodiments, the compartment is bonded to, welded or otherwise attached to assembly.

In some embodiments, the compartment may be created, following construction of a larger structure, comprising the structural elements, which may be processed and manipulated to form the assembly containing the compartment. For example, FIG. 3*a* depicts two porous structures 30 as part of the assembly 16 which assembly comprises a folding line 32, to create a fold between the two porous structures 30, as depicted. According to this aspect, and in one embodiment, one of the porous structures is so constructed, such that a depression in the assembly occurs, to form a cavity 34, which cavity is sized to be capable of holding a dry-powder there-within. FIG. 3*b* depicts a first step in the assembly of the formed compartment, in that the cover portion 38 containing one of the porous structures is folded over the second porous structure, containing the cavity 34, in which a dry powder 36 is then encased. FIG. 3*c* depicts the formed dry-powder containing compartment 19. In some embodiments, the compartment 19 thus formed is sealed against reopening by any means, for example by crimping the edges of the compartment 19 or by other closing means known in the art, such as ultrasonic welding, adhesion, spot welding, laser welding and others.

In some embodiments, the dry powder may comprise any therapeutic agent, for example, and in some embodiments, a drug or vaccine.

In some embodiments, any drug or drugs which may be administered by inhalation and which are either a solid or may be incorporated in a solid carrier are envisioned for incorporation within the inhalers, kits and/or methods of this invention. In some embodiments, the drug will be a drug for the treatment of a Respiratory disease or condition. In some embodiments, such drugs may comprise bronchodilators, corticosteroids and drugs for the prophylaxis of asthma. Other drugs such as anorectics, anti-depressants, anti-hypertensive agents, anti-neoplastic agents, anti-cholinergic agents, dopaminergic agents, narcotic analgesics, beta-adrenergic blocking agents, prostoglandins, sympathomimetics, tranquilizers, steroids, vitamins and/or hormones may be employed. Exemplary drugs include: Salbutamol, Terbutaline, Rimiterol, Fentanyl, Fenoterol, Pirbuterol, Reproterol, Adrenaline, Isoprenaline, Ociprenaline, Ipratropium, Beclomethasone, Betamethasone, Budesonide, Disodium Cromoglycate, Nedocromil Sodium, Ergotamine, Salmeterol, Fluticasone, Formoterol, Insulin, Atropine, Prednisolone, Benzphetamine, Chlorphentermine, Amitriptyline, Imipramine, Cloridine, Actinomycin C, Bromocriptine, Buprenorphine, Propranolol, Lacicortone, Hydrocortisone, Fluocinolone, Triamcinclone, Dinoprost, Xylometazoline, Diazepam, Lorazepam, Folic acid, Nicotinamide, Clenbuterol, Bitolterol, Ethinyloestradiol and Levenorgestrel.

Drugs may be formulated as a free base, one or more pharmaceutically acceptable salts or a mixture thereof.

The devices, kits and/or methods of the present invention may be particularly suitable to dispense dry powder substances to in vivo subjects, including animal and, typically, human subjects. The dry powder substance may include one or more active pharmaceutical constituents as well as biocompatible additives that form the desired formulation or blend.

As used herein, the term "dry powder" is used interchangeably with "dry powder formulation" and means the dry powder can comprise one or a plurality of constituents or ingredients with one or a plurality of (average) particulate size ranges.

In some embodiments, individual dispensable quantities of dry powder formulations can be a single ingredient or a plurality of ingredients, whether active or inactive. The inactive ingredients can include additives added to enhance flowability or to facilitate aerosolization delivery to the desired systemic target. The dry powder drug formulations can include active particulate sizes that vary.

The dry powder formulation can also include desired excipients. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

Examples of diseases, conditions or disorders that may be treated or prevented with the inhalers, kits and/or methods of the invention include, but are not limited to, asthma, COPD (chronic obstructive pulmonary disease), viral or bacterial infections, influenza, allergies, and other respiratory ailments as well as diabetes and other related insulin resistance disorders. The dry powder inhalant administration may be used to deliver locally acting agents such as antimicrobials, protease inhibitors, and nucleic acids/oligionucleotides as well as systemic agents such as peptides like leuprolide and proteins such as insulin.

For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or ogligonucleotides for cystic fibrosis gene therapy may be performed. See e.g. Wolff et al., Generation of Aerosolized Drugs, J. Aerosol. Med. pp. 89-106 (1994). See also U.S. Patent Application Publication No. 20010053761, entitled Method for Administering ASPB28-Human Insulin and U.S. Patent Application Publication No. 20010007853, entitled Method for Administering Monomeric Insulin Analogs, the contents of which are hereby incorporated by reference as if recited in full herein.

Typical dose amounts of the unitized dry powder mixture dispersed in the inhaler will vary depending on the patient size, the systemic target, and the particular drug. Typical doses that can be delivered by the inhaler range from 10 µg to 10 mg. Some additional exemplary dry powder drugs include, but are not limited to, albuterol, fluticasone, beclamethasone, cromolyn, terbutaline, fenoterol, β-agonists (including long-acting β-agonists), salmeterol, formoterol, cortico-steroids and glucocorticoids.

In certain embodiments, the administered bolus or dose can be formulated with an increase in concentration (an increased percentage of active constituents) over conventional blends. Further, the dry powder formulations may be configured as a smaller administrable dose compared to the conventional doses. For example, each administrable dry powder dose may be on the order of less than about 60-70% of that of conventional doses. In certain particular embodiments, using the active dispersal systems provided by certain embodiments of the DPI configurations of the instant invention, the adult dose may be reduced to under about 15 mg, such as between about 10 µg-10 mg. The active constituent(s) concentration may be between about 5-10%. In other embodiments, active constituent concentrations can be in the range of between about 10-20%, 20-25%, or even larger, up to the case where only pure drug is delivered.

In certain particular embodiments, during dose dispensing, the dry powder in a particular dose receptacle may be formulated as an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

In some embodiments, the therapeutic agent can be a biologic, which includes but is not limited to proteins, polypeptides, carbohydrates, polynucleotides, and nucleic acids. In some embodiments, the protein can be an antibody, which can be polyclonal or monoclonal. In some embodiments, the therapeutic can be a low molecular weight molecule. In addition, the therapeutic agents can be selected from a variety of known pharmaceuticals such as, but are not limited to: analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, antacids, antidiarrheals, antidotes, antifolics, antipyretics, antirheumatic agents, psychotherapeutic agents, neural blocking agents, anti-inflammatory agents, antihelmintics, anti-arrhythmic agents, antibiotics, anticoagulants, antidepressants, antidiabetic agents, antiepileptics, antifungals, antihistamines, antihypertensive agents, antimuscarinic agents, antimycobacterial agents, antimalarials, antiseptics, antineoplastic agents, antiprotozoal agents, immunosuppressants, immunostimulants, antithyroid agents, antiviral agents, anxiolytic sedatives, bone and skeleton agents, astringents, beta-adrenoceptor blocking agents, cardiovascular agents, chemotherapy agents, corticosteroids, cough suppressants, diagnostic agents, diagnostic imaging agents, diuretics, dopaminergics, enzymes and enzyme cofactors, gastrointestinal agents, growth factors, hematopoietic or thrombopoietic factors, hemostatics, hematological agents, hemoglobin modifiers, hormones, hypnotics, immunological agents, antihyperlipidemic and other lipid regulating agents, muscarinics, muscle relaxants, parasympathomimetics, parathyroid hormone, calcitonin, prostaglandins, radio pharmaceuticals, sedatives, sex hormones, anti-allergic agents, stimulants, steroids, sympathomimetics, thyroid agents, therapeutic factors acting on bone and skeleton, vasodilators, vaccines, vitamins, and xanthines. Antineoplastic, or anticancer agents, include but are not limited to paclitaxel and derivative compounds, and other antineoplastics selected from the group consisting of alkaloids, antimetabolites, enzyme inhibitors, alkylating agents and antibiotics.

Exemplary proteins, include therapeutic proteins or peptides, or carrier proteins or peptides, including GCSF; GMCSF; LHRH; VEGF; hGH; lysozyme; alpha-lactoglobulin; basic fibroblast growth factor basic fibroblast growth factor; (bFGF); asparaginase; tPA; urokin-VEGF; chymotrypsin; trypsin; streptokinase; interferon; carbonic anhydrase; ovalbumin; glucagon; ACTH; oxytocin; phosphorylase b; secretin; vasopressin; levothyroxin; phatase; beta-galactosidase; parathyroid hormone, calcitonin; fibrinogen; polyaminoacids (e.g., DNAse, alphal antitrypsin; polylysine, polyarginine); angiogenesis inhibitors or pro-immunoglobulins (e.g., antibodies); somatostatin and analogs thereof; casein; collagen; soy protein; and cytokines (e.g., interferon, interleukin and others); immunoglobulins.

Exemplary hormones and hormone modulators include proinsulin, C-peptide of insulin, a mixture of insulin and C-peptide of insulin, hybrid insulin cocrystals, growth hormone, parathyroid hormone, luteinizing hormone-releasing hormone (LH-RH), adrenocorticotropic hormone (ACTH), amylin, oxytocin, luteinizing hormone, (D-Tryp6)-LHRH, nafarelin acetate, leuprolide acetate, follicle stimulating hormone, glucagon, prostaglandins, steroids, estradiols, dexamethazone, testosterone, and other factors acting on the genital organs and their derivatives, analogs and congeners.

Exemplary hematopoietic or thrombopoietic factors include, among others, erythropoietin, granulocyte colony stimulating factor (G-CSF), granulocyte-macrophage stimulating factor (GM-CSF) and macrophage colony stimulating factor (M-CSF), leukocyte proliferation factor preparation, thrombopoietin, platelet proliferation stimulating factor, megakaryocyte proliferation (stimulating) factor, and factor VIII.

Exemplary therapeutic factors acting on bone and skeleton and agents for treating osteoporosis include calcium, alendronate, bone GLa peptide, parathyroid hormone and its active fragments, histone H4-related bone formation and proliferation peptide and their muteins, derivatives and analogs thereof.

Exemplary enzymes and enzyme cofactors include: pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, and superoxide dismutase (SOD).

Exemplary vaccines include Hepatitis B, Influenza, MMR (measles, mumps, and rubella), and Polio vaccines and others.

Exemplary growth factors include nerve growth factors (NGF, NGF-2/NT-3), epidermal growth factor (EGF), fibroblast growth factor (FGF), insulin-like growth factor (IGF), transforming growth factor (TGF), platelet-derived cell growth factor (PDGF), hepatocyte growth factor (HGF) and so on.

Exemplary agents acting on the cardiovascular system include factors which control blood pressure, arteriosclerosis, etc., such as endothelins, endothelin inhibitors, endothelin antagonists, endothelin producing enzyme inhibitors vasopressin, renin, angiotensin I, angiotensin II, angiotensin III, angiotensin I inhibitor, angiotensin II receptor antagonist, atrial naturiuretic peptide (ANP), antiarrythmic peptide and so on.

Exemplary factors acting on the central and peripheral nervous systems include opioid peptides (e.g. enkephalins, endorphins), neurotropic factor (NTF), calcitonin gene-related peptide (CGRP), thyroid hormone releasing hormone (TRH), salts and derivatives of TRH, neurotensin and so on.

Exemplary chemotherapeutic agents, such as paclitaxel, mytomycin C, BCNU, and doxorubicin.

Exemplary agents acting on the respiratory system include factors associated with asthmatic responses, e.g., albuterol, fluticazone, ipratropium bromide, beclamethasone, and other beta-agonists and steroids.

Exemplary steroids include but are not limited to beclomethasone (including beclomethasone dipropionate), fluticasone (including fluticasone propionate), budesonide, estradiol, fludrocortisone, flucinonide, triamcinolone (including triamcinolone acetonide), and flunisolide. Exemplary beta-agonists include but are not limited to salmeterol xinafoate, formoterol fumarate, levo-albuterol, bambuterol, and tulobuterol.

Exemplary anti-fungal agents include but are not limited to itraconazole, fluconazole, and amphotericin B.

Numerous combinations of active agents may be desired including, for example, a combination of a steroid and a beta-agonist, e.g., fluticasone propionate and salmeterol, budesonide and formoterol, etc.

The assemblies of this invention may comprise, in some embodiments, one or more compartments, with each compartment comprising a dry-powder. In some embodiments, when the assemblies comprise more than one compartment, each compartment may comprise the same or different dry-powders.

In some embodiments, the assembly comprises two or three compartments containing a dry-powder. According to this aspect, and in some embodiments, the two or three compartments comprise two or three different dry-powders.

In some embodiments, the assembly comprises a compartment containing at least one or two partitions, which partitions create separate chambers in the compartment. According to this aspect, and in some embodiments, the separate chambers may contain different dry-powders.

The inhalers, kits and/or methods of the present invention, inter alia is well suited to deliver two or more inhaled dry-powder drugs simultaneously while storing them separately. In some embodiments, according to this aspect, a technical challenge in the inhaler industry involving the storage of two or more drugs, which is potentially problematic for both chemical and regulatory reasons, is obviated by certain embodiments of this invention.

From a chemical perspective, the co-storage of two or more drugs within the same physical compartment can be problematic as the two drugs may interact, especially if they have different pHs. From a regulatory standpoint, it may be necessary to prove that there is no such interaction over a long time period, and this can add significant expense to the regulatory approvals process.

Figure 3A:
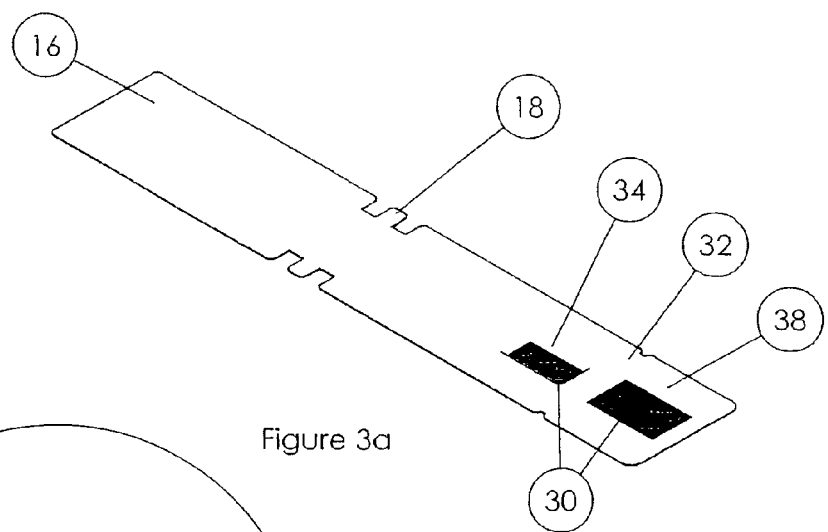
FIG. 3*a* provides an isometric view of an embodiment of an assembly of this invention, showing a single-compartment design, appropriate for containing one drug.
Figure 3B:
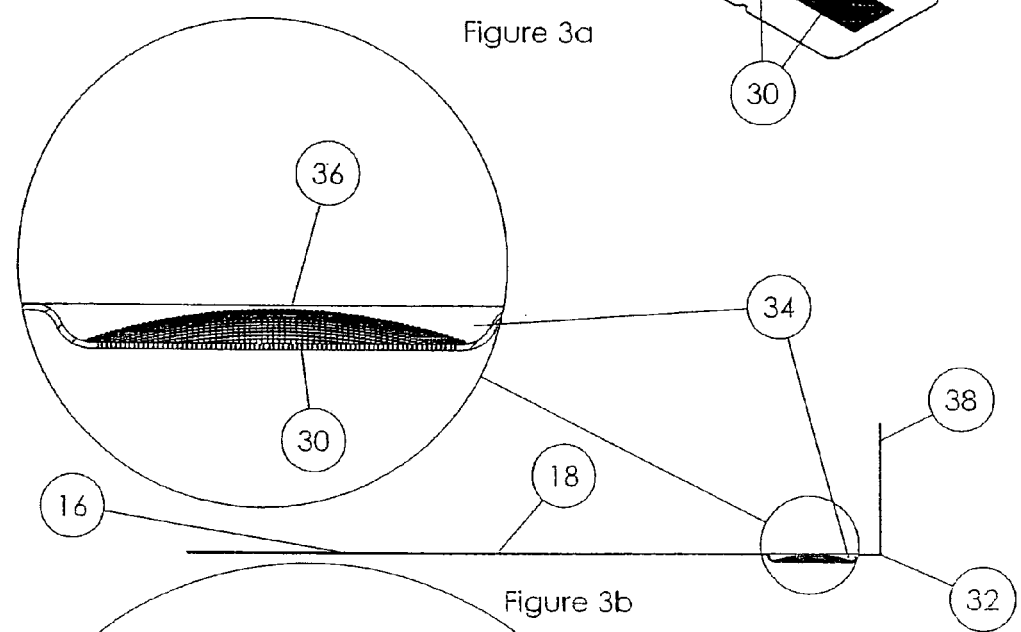
FIG. 3*b* shows a cross-sectional view of an embodiment of an assembly of this invention, prior to closing the porous compartment.
Figure 3C:
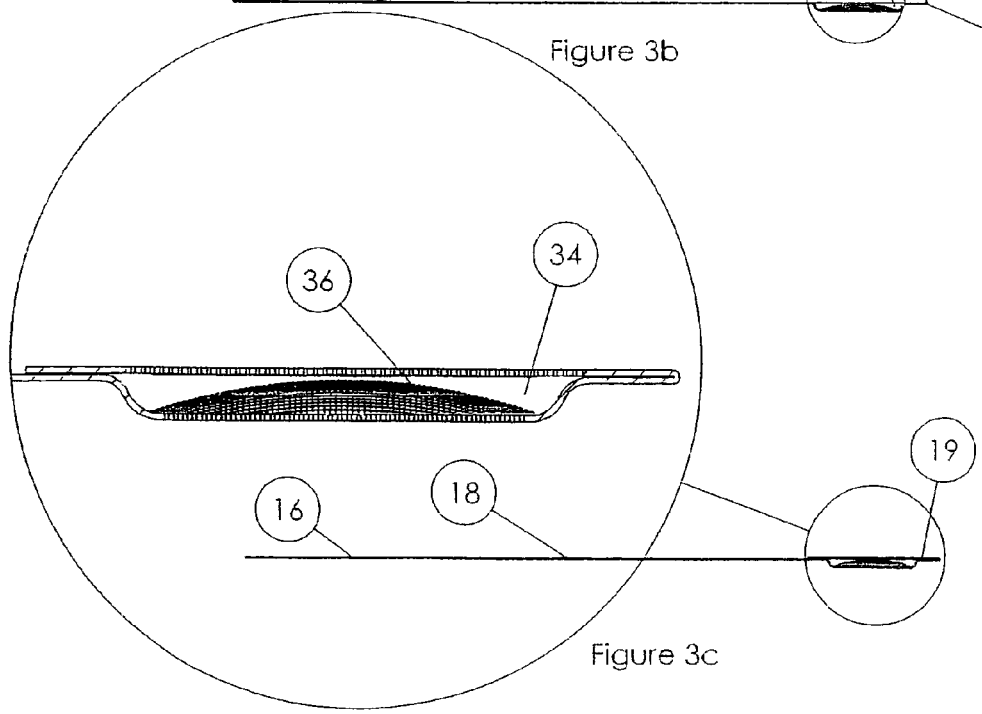

FIG. 4 depicts another embodiment of this invention, wherein, in a design similar to that shown in FIG. 3, the embodied device of FIG. 4 can be used to package two drugs within separate compartments or chambers, contained within the assembly 16.

Figure 4A:
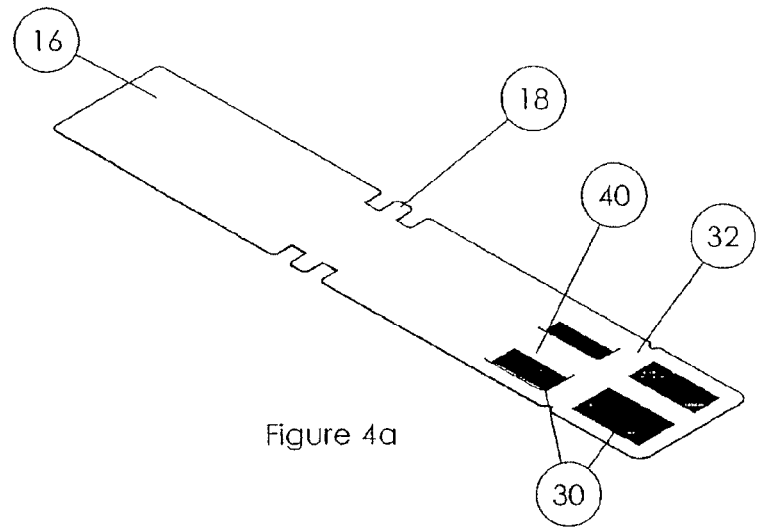
FIG. 4*a* provides an isometric view of an embodiment of an assembly of this invention, showing a double-compartment design, appropriate for delivering two drugs simultaneously.
Figure 4B:
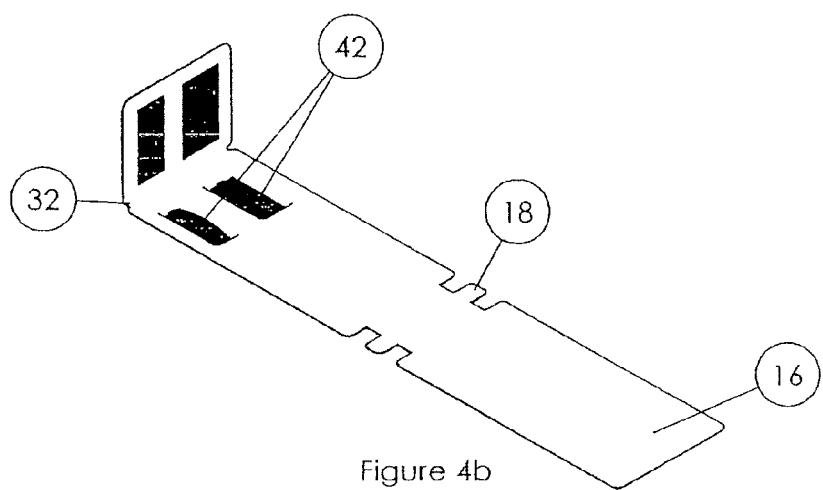
FIG. 4*b* shows a cross-sectional view of an embodiment of an assembly of this invention, prior to closing the two porous compartments.
Figure 4C:
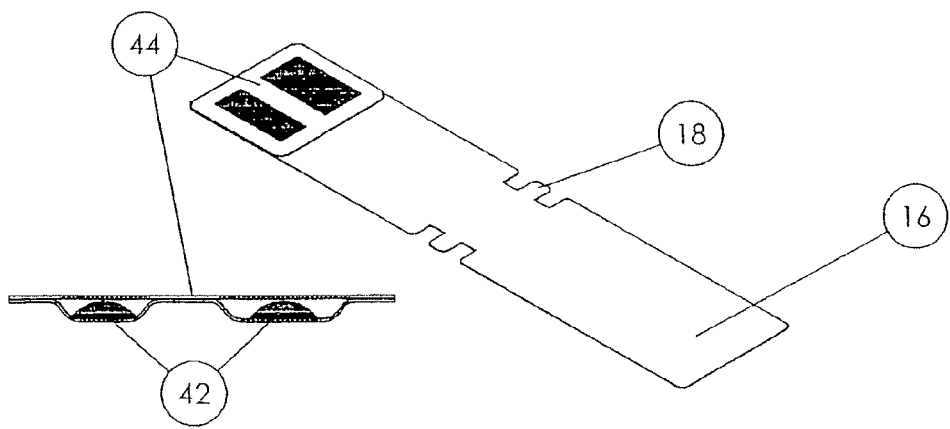
FIG. 4*c* shows a cross-sectional view of an embodiment of an assembly of this invention, subsequent to closing the two porous compartments.

FIG. 4a depicts a double-cavity area 40 created by the fold-over of one porous structure onto another 30. As shown in FIG. 4b, the double-cavity 40 enables the containment of two separate drugs 42 one within each compartment. FIG. 4c shows these two drugs 42 stored within the double-compartment 44 created by the sealing or closure of the compartments created in the fold-over depicted in FIG. 4b.

The principle of operation of an embodied device of this invention is depicted in FIG. 2. A number of different possible states of the assembly 16 within the casing 10 are shown, as the assembly partially rotates back and forth due to an inhalation action, at the powder delivery port 12, which may be facilitated by the incorporation of a mouthpiece at its end. FIG. 2a shows a state in which the assembly is not blocking the airflow through the casing 10. Without wishing to be bound by theory, the off-center positioning of the air inlet 14 creates turbulence in the area 20 between the inlet 14 and the portion 22 of the assembly 16 proximal to the inlet. According to this aspect, the assembly is tipped by the turbulence into one of the states shown in FIGS. 2b and 2c. Referring now to FIG. 2b, the assembly end 22 proximal to the air inlet 16, lowers, raising the assembly end distal to the air inlet 24, resulting in some blocking of the airflow through the device. In one embodied mechanism, the airflow (shown as "A") causes the assembly to partially rotate or rock in the direction shown by the arrow marked "R", which in turn causes the assembly 16 to partially rotate in an opposing direction, or flip to the configuration shown in FIG. 2c. Such partial rotation or flipping, may cycle, i.e. the airflow ("A") may cause the assembly to flip back to its former state. In this way, the airflow through the device may cause the assembly 16 to repeatedly rotate between the two states. Each time this occurs, the assembly end 24, comprising the dry-powder containing compartment distal to the air inlet 16 beats against an internal surface 26 of the casing 10, causing the drug powder (not shown) within the porous compartment 19 to be released gradually from such compartment 19.

Figure 2A:
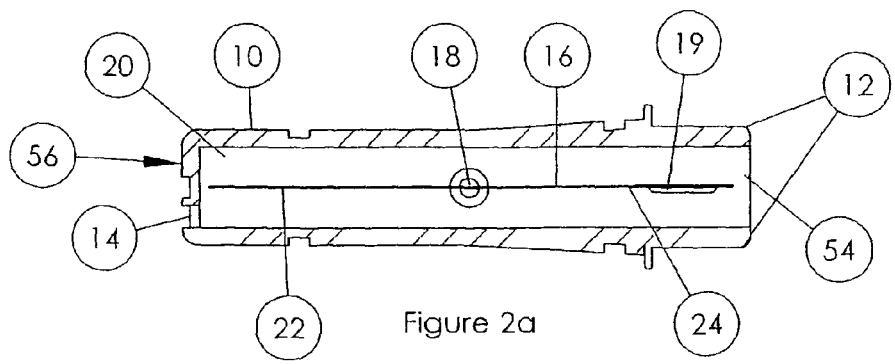
FIG. 2*a* shows a cross-sectional view of an embodied device, wherein the assembly is not blocking the airflow through said device.
Figure 2B:
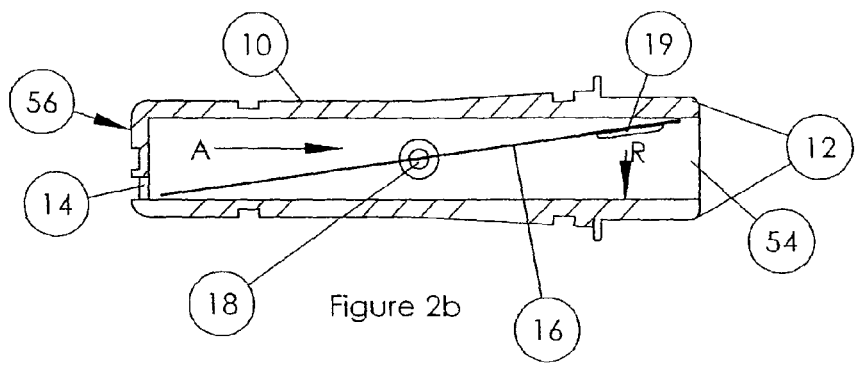
FIG. 2*b* provides a cross-sectional view of an embodied device wherein the end of the assembly proximal to the inlet may block the airflow through said device.
Figure 2C:
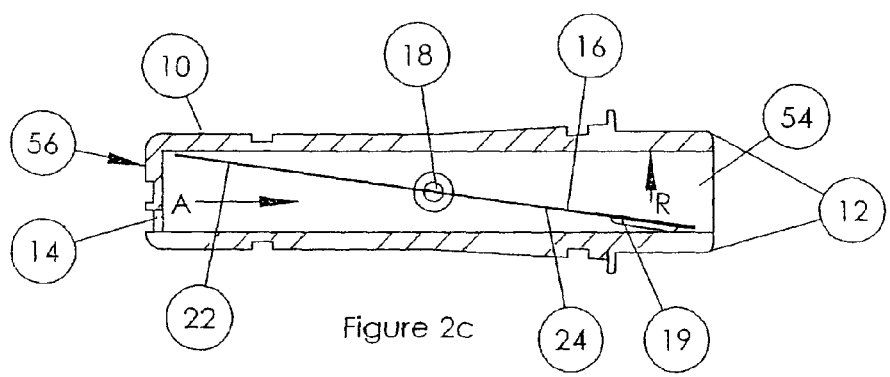
FIG. 2*c* provides a cross-sectional view of an embodied device wherein the end of the assembly distal to the inlet may block the airflow through the device.
Figure 2D:
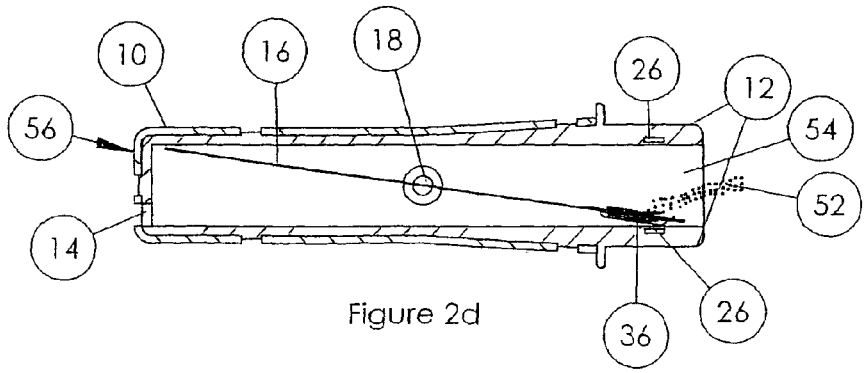
FIG. 2*d* provides a further cross-sectional view of an embodied inhaler, showing some of the powder emerging from the porous compartment of the inhaler as the assembly impacts against an interior surface of the inhaler.

FIG. 2d, further depicts an aspect of the mechanism for dry powder release from an embodied inhaler device of this invention. Following repeat partial rotations, resulting in beating of the dry-powder containing compartment distal to the air inlet against an internal surface 26 of the casing, the powder 36 contained within the porous compartment emerges as free powder 52 into the airflow, which is drawn towards the powder delivery port 12. Without wishing to be bound by theory, as this powder 52 emerges, it is disaggregated as a result of the sieving action of the pores of the compartment. In one embodiment, such hole size for disaggregation to achieve drug powder particles in the 1-5 micron diameter range is in the 10 micron to 70 micron range.

In one embodiment, the inhaler devices of this invention may be so constructed such that at certain regions of the interior of the casing, a protrusion may be effected, such that upon partial rotation of the assembly, the porous compartment will strike the interior surface at a region of such protrusion, facilitating release of the dry-powder contained therein. Referring again to FIG. 2D), protruding surfaces 26 are shown extending from an interior surface of the casing 10. According to this aspect, such protrusions are so positioned such that the porous compartment 19 specifically strikes the protruding surface 26.

In some embodiments, such partial rotation, rocking or flipping of the assembly within the casing is accomplished due to a unique fitting of a lateral extension of the assembly, for example, 18 in FIG. 1b, within an appropriate housing, for example, 15 in FIG. 1b. In some embodiments, such housing may also comprise a slit or rounded hole through the casing, into which such lateral extension may insert. It is to be appreciated that any modification of the assembly to allow for positioning of the assembly within the casing and facilitating partial rotation of the assembly is to be considered as part of this invention.

In some embodiments, when the assembly comprises two or more chambers or compartments, the assembly may strike the protruding surface at a region between the two chambers or compartments, or in some embodiments, the interior surface may comprise multiple protruding surfaces such that each chamber or compartment will strike the interior surface at a region containing a protruding surface.

In some embodiments, the composition of the protruding surface may be so selected to impart desired characteristics, for optimal dry-powder release. For example, beating against a plastic surface may create a damping effect, and in this case the use of a metallic beating surface instead may produce a sharper beating.

In some embodiments, the invention provides for a method of dispensing dry powder from an inhaler, comprising facilitating airflow through a dry-powder inhaler device including any single or combined embodiments described herein, to cause the assembly to partially rotate within the casing about a single axis and thereby release dry-powder from the compartment to become entrained in the airflow, thereby dispensing dry powder from the inhaler. FIG. 2 depicts an embodiment whereby a principle of operation of an embodied device of this invention results in the dispensing of a dry-powder from an inhaler of this invention, which represents an aspect of the methods of this invention.

The inhaler devices of this invention may be single use devices, which are preloaded with a desired dry-powder agent, at a desired dosage.

In some embodiments, according to this aspect, care is taken to ensure appropriate dry-powder containment within the porous compartments of the inhaler devices of this invention, prior to or between use of the inhaler device.

FIG. 5 depicts an embodiment whereby such care is taken. According to this aspect, and in one embodiment, the device further comprises an immobilizer cap, which immobilizer cap attaches to the powder delivery port and which immobilizer cap prevents substantial rotation of the assembly about an axis.

FIG. 5a shows an embodiment of an inhaler further comprising an immobilizer cap. According to this aspect, and in one embodiment, as seen in the cross-sectional view of the inhaler depicted, a device of this invention may appear in its immobilized state; i.e. on removal from blister or other packaging. In this state, a cap 50 serves to constrain the movement of the assembly 16 from any substantial rotation or movement, and thus prevents beating (and drug powder release) from occurring.

In one embodiment, and in order to function as an effective shock absorber, the cap may comprises a foam, rubber or sponge-like material such as Santoprene™ on an interior surface, which comes into proximity with the compartment containing a dry-powder. The state of the inhaler after removal of the cap 50 is shown in depicted in FIG. 2b. At this point, the assembly 16 is free to move, and may partially rotate, as described herein, once inhalation action commences.

It will be evident to those skilled in the art that the invention is not limited to the details of the foregoing illustrative embodiments and that the present invention may be embodied in other specific forms without departing from the spirit or essential attributes thereof.

The embodiments presented herein are therefore to be considered in all respects as illustrative and not restrictive of the scope of the invention, and the skilled artisan will appreciate the appropriate equivalents thereto, which are to be considered as part of this invention.

What is claimed is:

1. A dry-powder inhaler device comprising:
   a casing;
   an air inlet located at a first terminus of said casing;
   a powder delivery port located at a second terminus of said casing, which powder delivery port is positioned distal to said air inlet; and
   an elongated assembly located within an interior of said casing, wherein:

a first terminus of said elongated assembly is located proximally to said air inlet;

a second terminus of said elongated assembly is located proximally to said powder delivery port;

said elongated assembly is fitted within said casing such that said elongated assembly partially rotates within said casing about a single axis; and said elongated assembly comprises at least one compartment containing a dry-powder, wherein said compartment containing a dry-powder is located proximally to said second terminus of said elongated assembly; and said compartment containing a dry-powder comprises a porous structure encasing said dry-powder;

whereby airflow through said device causes said elongated assembly to and rock back and forth within said casing about the single axis and to beat against said casing, and whereby dry-powder is thereby released from said compartment and becomes entrained in said airflow.

2. The dry-powder inhaler device of claim 1, wherein said casing, said elongated assembly, or a combination thereof is substantially rectangular.

3. The dry-powder inhaler device of claim 1, wherein said inlet is positioned to be off center of a horizontal axis, a vertical axis or a combination thereof of a side of said casing containing said inlet.

4. The dry-powder inhaler device of claim 1, wherein said casing comprises a housing into which a portion of a side of said elongated assembly inserts, which facilitates the partial rotation of said elongated assembly within said casing.

5. The dry-powder inhaler device of claim 1, wherein said porous structure has a pore size ranging from about 20 to about 50 microns.

6. The dry-powder inhaler device of claim 1, wherein said porous structure is a mesh-like structure.

7. The dry-powder inhaler device of claim 1, wherein said elongated assembly comprises a metal or metal foil.

8. The dry-powder inhaler device of claim 1, wherein said elongated assembly comprises two or three compartments containing a dry-powder.

9. The dry-powder inhaler device of claim 8, wherein said two or three compartments house two or three different dry-powders.

10. The dry-powder inhaler device of claim 1, wherein said compartment containing a dry-powder contains at least two partitions, which partitions create separate chambers in said compartment.

11. The dry-powder inhaler device of claim 10, wherein said separate chambers contain different dry-powders.

12. The dry-powder inhaler device of claim 1, wherein said casing further comprises a mouthpiece attached to or comprising said powder delivery port.

13. The dry-powder inhaler device of claim 1, wherein said dry powder comprises a therapeutic agent.

14. The dry-powder inhaler device of claim 1, wherein said therapeutic agent is a drug or a vaccine.

15. The dry-powder inhaler device of claim 1, further comprising an immobilizer cap, which immobilizer cap attaches to said powder delivery port and which immobilizer cap prevents substantial rotation of said elongated assembly about said single axis.

16. A kit comprising at least one dry-powder inhaler device of claim 1 and one or more mouthpieces, which mouthpieces may attach to said powder delivery port of said device.

17. The kit of claim 16, wherein said kit contains a number of said dry-powder inhaler devices equal to a desired dosage regimen.

18. A method of dispensing dry powder from an inhaler, comprising facilitating airflow through the dry-powder inhaler device of claim 1 to cause said elongated assembly to partially rotate within said casing about the single axis and thereby release dry-powder from said compartment to become entrained in said airflow, thereby dispensing dry powder from the inhaler.

* * * * *